(12) United States Patent
Haveri

(10) Patent No.: US 8,194,249 B2
(45) Date of Patent: Jun. 5, 2012

(54) GAS ANALYZER

(75) Inventor: Heikki Haveri, Huhmari (FI)

(73) Assignee: General Electric Company, Schenectady, NY (US)

( * ) Notice: Subject to any disclaimer, the term of this patent is extended or adjusted under 35 U.S.C. 154(b) by 236 days.

(21) Appl. No.: 12/697,324

(22) Filed: Feb. 1, 2010

(65) Prior Publication Data

US 2010/0208268 A1     Aug. 19, 2010

(30) Foreign Application Priority Data

Feb. 18, 2009  (EP) ..................................... 09396002

(51) Int. Cl.
  *G01N 33/497*  (2006.01)
(52) U.S. Cl. ......... 356/437; 356/432; 356/244; 356/246
(58) Field of Classification Search .................. 356/244, 356/246, 432–444; 250/343, 341.3, 338.5
See application file for complete search history.

(56) References Cited

U.S. PATENT DOCUMENTS

| | | | |
|---|---|---|---|
| 4,370,553 A | 1/1983 | Waycaster et al. | |
| 5,044,747 A | 9/1991 | Anthony | |
| 5,129,401 A | 7/1992 | Corenman et al. | |
| 5,153,436 A * | 10/1992 | Apperson et al. | 250/345 |
| 5,282,473 A * | 2/1994 | Braig et al. | 600/532 |
| 5,585,635 A * | 12/1996 | Graham | 250/343 |
| 5,610,400 A * | 3/1997 | Weckstrom | 250/345 |
| 5,621,213 A * | 4/1997 | Barshad | 250/373 |
| 6,147,351 A * | 11/2000 | Huiku | 250/343 |
| 6,279,378 B1 * | 8/2001 | Sheen et al. | 73/24.01 |
| 6,527,398 B1 * | 3/2003 | Fetzer | 356/437 |
| 7,183,552 B2 * | 2/2007 | Russell | 250/338.5 |
| 2008/0035848 A1 * | 2/2008 | Wong | 250/345 |

* cited by examiner

*Primary Examiner* — Sang Nguyen
(74) *Attorney, Agent, or Firm* — Global Patent Operation; Jonathan E. Thomas

(57) ABSTRACT

A gas analyzer is disclosed herein. The gas analyzer includes a light source for transmitting a radiation and a sampling chamber having a first opening for receiving a gas sample, a second opening for removing the gas sample, at least one optical window towards the radiation allowing the radiation to traverse the gas sample and also having a first wall and a second wall opposite to the first wall, the first wall and second wall edging the sampling chamber to guide the gas sample from the first opening to the second opening. The gas analyzer also includes at least one detector for receiving the radiation after traversing the gas sample. The first wall and the second wall of the sampling chamber is curved and at a predetermined distance from each other, an overall shape of the second wall being mostly similar to the first wall.

18 Claims, 4 Drawing Sheets

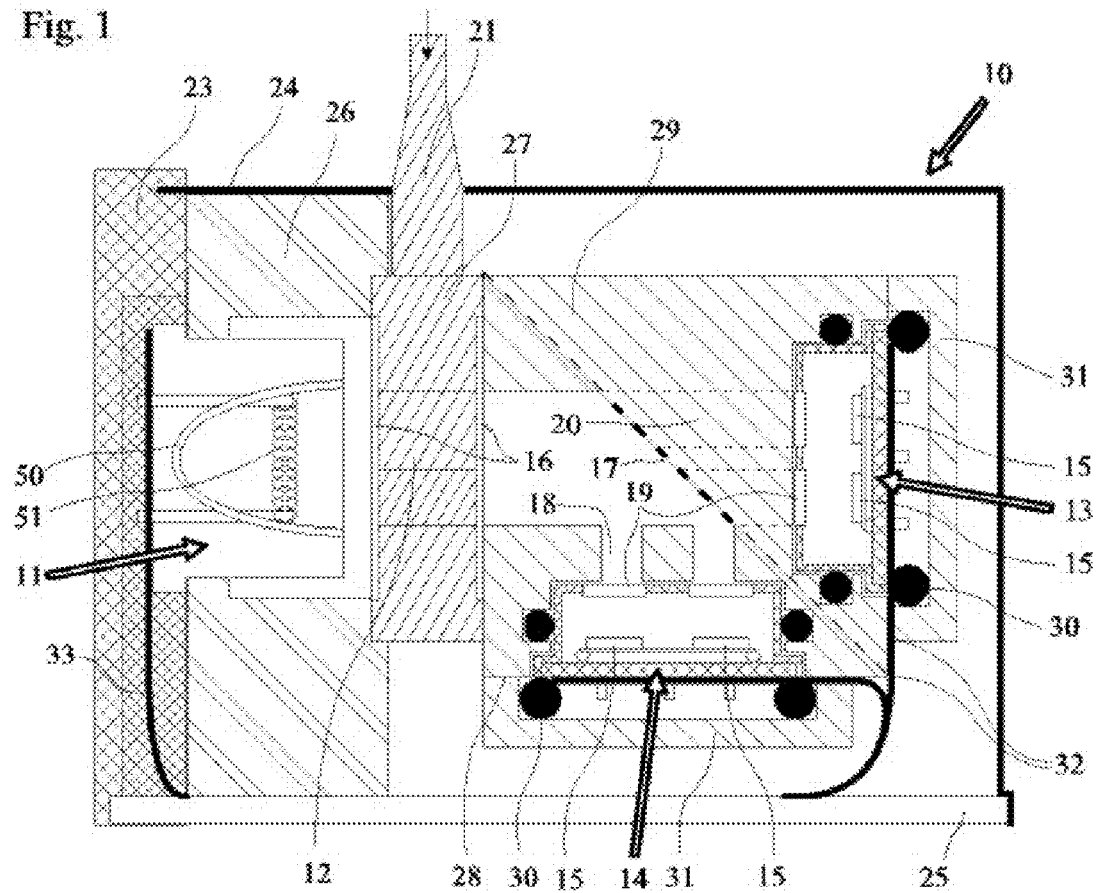

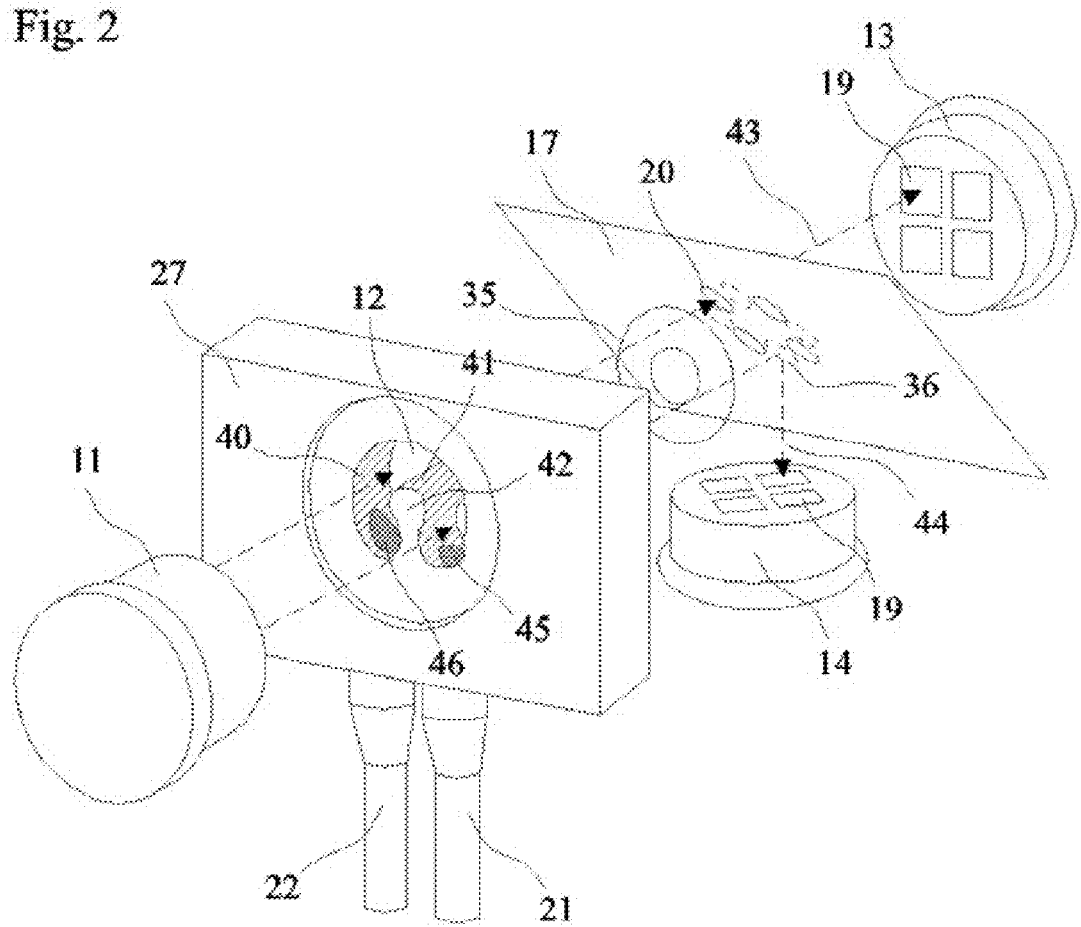

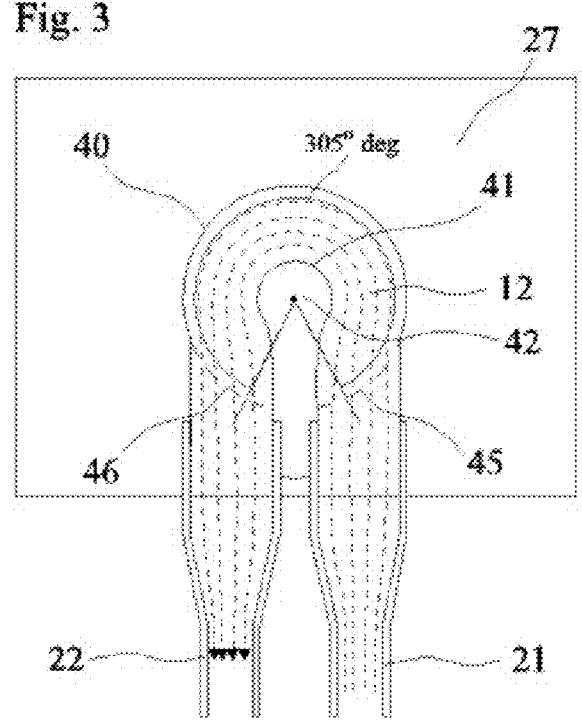
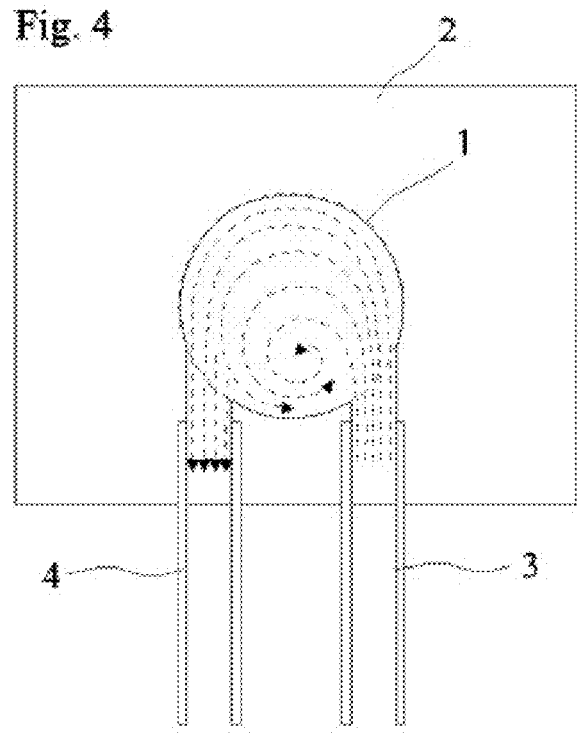
Prior art

GAS ANALYZER

CROSS-REFERENCE TO RELATED APPLICATIONS

This application claims priority under 35 U.S.C. §119(a)-(d) or (f) to prior-filed, co-pending European patent application serial number 09396002.9, filed on Feb. 18, 2009, which is hereby incorporated by reference in its entirety.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO A SEQUENCE LISTING, A TABLE, OR COMPUTER PROGRAM LISTING APPENDIX SUBMITTED ON COMPACT DISC

Not Applicable

BACKGROUND OF THE INVENTION

1. Field of the Invention

This disclosure relates generally to a gas analyzer comprising a light source, a sampling chamber and at least one detector.

2. Description of Related Art

Conventionally it has been adequate enough to measure a gas concentration at steady states only, however, continuous, real time gas analyzing is becoming more and more important in different kind of applications. To measure fast gas concentration changes during different transients also a response time of an analyzer should be quick enough, both in an electric and pneumatic sense. It is also desired to measure more than one gas component of a gas mixture at once.

A breath by breath concentration measurement of different respiratory gases is one of the most demanding forms of a gas measurement. A human can breath spontaneously up to 200 breaths per minute, but a patient can be ventilated mechanically close to thousand breaths per minute as well. However, the high frequency ventilation is more like a vibration and a diffusion of gas molecules and the outcome looks more like a constant gas concentration rather than a breath to breath alternating signal. The gas concentration of $CO_2$, that the patient produces, is normally around five volume percents at an end of an expiration, thus with a healthy patient the concentration of $CO_2$ varies from 0 to 5 volume percents between the inspiration and the expiration. A time used for the inspiration is usually shorter, only one third, compared to a time used for the expiration, which is two thirds of the breathing cycle. This means that the possible steady state time of the concentration at the end of the inspiration is smaller compared to that of the expiration. As a frequency of breathing increases the steady state time of the gas concentration also decreases proportionally. In addition a breathing system mechanics starts to affect shortening the time even more although the gas concentration change between the inspiration and the expiration at an alveoli deep in the lungs is fast.

The gas concentration curve drawn according to the change of the inspiration and the expiration would look like a square wave inside bronchiole just by the alveoli. However, since the inspired and expired gases mix as they travel back and worth within the inspiration and the expiration through the dead space of bronchioles, bronchi, bronchus, trachea, endotracheal tube, part of the breathing circuit and finally through different connectors in to the analyzer located outside the patient the concentration curve at the analyzer input would look more like a filtered square wave with rounded corners. As the frequency of breathing is increased the breathing volume decreases proportionally, if the ventilator working pressure is maintained constant, which in turn increases the mixing of the inspired and expired gases in the dead space even more, since smaller amounts of gases move inside relatively larger dead space.

Gas samples of respiratory gases are sucked from the breathing circuit in to the analyzer through a sample gas tube. Inside the analyzer gas samples are processed to get a continuous, real time gas concentration waveform, of course with a small processing delay. At this point, especially with higher breathing frequencies, the waveform looks more like a sine wave because of the further mixing of inspiratory and expiratory gas samples inside the analyzer. If more gases in addition to for example CO2 is measured the processing of gas samples may mix the gas even more also worsening the signal. It is also desirable to keep the sample gas flow as small as possible so that the actual process that is being measured is not disturbed too much. Lowering of the sample gas flow increases the analyzer response time dramatically since mixing of sample gases, caused by diffusion, turbulences and inertia near the walls in accordance with a laminar flow, increase as they spend more time flowing through the sample gas tube in to the analyzer, but also inside the analyzer as the sample is processed. Thus noticing what is explained above with conventional techniques used to measure gas concentrations in respiratory care it is possible to measure different breathing gas concentrations continuously, in real time, up to 20-40 breathes per minute only depending on the measured gas.

The response time of the analyzer can be expressed in terms of a rise time and a fall time that helps to understand better the functioning of the analyzer in time sense. The rise time is the time in which the gas analyzer output signal changes its state from 10% to 90% level of its total signal change as the gas concentration in the analyzer input changes from the constant lower gas concentration level to the constant higher gas concentration level.

The analyzer rise/fall time is basically a combination of the rise/fall times of an electrical circuitry and a pneumatic system. The analyzer rise/fall time can be described with a simplified equation $\tau=\sqrt{X^2+Y^2}$, in which X is a total electrical rise/fall time and Y is a total pneumatic rise/fall time. Normally some material in connection with the measured gases cause additional increase into rise/fall time as they may absorb and emit gas molecules. To mention other things also the viscosity of gases may increase or decrease rise/fall time. The total electrical rise/fall time is similarly expressed with an equation $\tau=\sqrt{X_1^2+X_2^2+...}$, where $X_1, X_2$ . . . are rise/fall times of each electrical components such as a detector that transforms an infrared radiation in to an electrical voltage proportional to the gas concentration or electrical filters used to filter a noise from the signal produced by the detector or amplifiers etc. A length, shape and smoothness of a flow path, through which the sample gas flows from a location where the sample was taken in to a place where it is analyzed, causes increase in the pneumatic rise/fall time. The total pneumatic rise/fall time can be expressed with an equation $\tau=\sqrt{Y_1^2+Y_2^2+...}$, where $Y_1, Y_2$ . . . are rise/fall times of each pneumatic components such as mechanical connections that are step like changes with an additional space along the flow path or just sharp corners or some kind of flow barriers such as filters etc. Usually the pneumatic design of the analyzer system is more dominant thus the effect of the electrical rise/fall time X is smaller than the effect of the pneumatic rise/fall time Y in the equation of the analyzer rise/fall time.

The flow speed of the sample gas through the pneumatic system has an influence on the rise/fall time also. The longer the sample gas travels through the small tubing and cavities inside the analyzer the more the gas samples containing different gas concentrations mix up. On the other hand in many cases it would be desirable to "steal" as little sample gas as possible from the primary system to be analyzed at the analyzer. Such a low sampling flow the gas analyzer is challenging to implement since the sensor rise/fall time increase as the sample flow is decreased. This in turn makes the gas concentration measurement at higher transition frequencies even more difficult.

A sampling chamber, where the sampled gas is analyzed and which enables the concentration measurement of even seven different gas components from the one gas mixture, is one of the most dominant pneumatic components which increases the pneumatic system rise/fall time of the gas analyzers.

A cross sectional view of a conventional sampling chamber 1 inside a housing 2 is shown in FIG. 4 from a direction of a radiation source (not shown) to a detector (not shown). The sampling chamber 1 is cylindrical when looked from the direction of radiation source, but rectangular when looked from aside. An inlet tube 3 and an outlet tube 4 are straight. The sample gas flows to the sampling chamber 1 through inlet tube 3 in to the direction of dotted lines that show how the gas flows through the sampling chamber and out from the sampling chamber through the outlet tube 4. The step like change in the flow path from the inlet tube 3 in to the sampling chamber 1 causes a turbulence inside the sampling chamber aside exit of the inlet tube (not shown in the figure), which mixes up the gas flow. The gas flowing through the cavity causes a strong turbulence or curl in to the middle of the sampling chamber also, which mixes up the new gas entering the chamber with the gas already inside the chamber circulating within the curl. This slows down the rise/fall time of the sampling chamber considerably. A reason for the turbulence is the fact that when the gas sample is discharged from the narrow inlet tube 3 to a large volume of the sampling chamber 1 gas molecules of the gas sample try if allowed to fill a larger volume and obtain more room inside the sampling chamber. Then the flow cannot be any more laminar, which is desired for keeping the gas concentration also inside the sampling chamber as unchanged as possible corresponding to a real situation when the sample was actually taken. Since the sampling chamber is just the place where the radiation traverses through the sample gas and traversed radiation is finally received by the detector for analysis, turbulences especially inside the sampling chamber have a very negative impact on analysis results.

BRIEF SUMMARY OF THE INVENTION

The above-mentioned shortcomings, disadvantages and problems are addressed herein which will be understood by reading and understanding the following specification.

In an embodiment, a gas analyzer includes a light source for transmitting a radiation. The gas analyzer also includes a sampling chamber having a first opening for receiving a gas sample and having a second opening for removing the gas sample and at least one optical window towards the radiation allowing the radiation to traverse the gas sample and also having a first wall and a second wall opposite to the first wall, the first wall and second wall edging the sampling chamber to guide the gas sample from the first opening to the second opening. The gas analyzer further includes at least one detector for receiving the radiation after traversing the gas sample. The first wall and the second wall of the sampling chamber is curved and at a predetermined distance from each other, an overall shape of the second wall being mostly similar to the first wall.

In another embodiment, a gas analyzer includes a light source for transmitting a radiation towards at least one direction. The gas analyzer also includes a sampling chamber having a first opening to receive a gas sample, a second opening to remove the gas sample, planar optical windows at a predetermined distance from each other allowing the radiation traverse through both optical windows and the gas sample therebetween and also having a first wall and a second wall opposite to the first wall, the first wall and second wall together with the optical windows to edge the sampling chamber to guide the gas sample from the first opening to the second opening. The gas analyzer further includes at least one detector to receive the radiation after traversing the gas sample. The first wall and the second wall of the sampling chamber is curved and at a predetermined distance from each other, the first wall and the second wall being substantially parallel.

In yet another embodiment a gas analyzer includes a light source for transmitting a radiation towards at least one direction. The gas analyzer also includes a sampling chamber having a first opening to receive a gas sample and having a second opening to remove the gas sample and at least one optical window towards the at least one direction of the radiation to allow the radiation to traverse the gas sample and also having a first wall and a second wall opposite to the first wall, the first wall and second wall to edge the sampling chamber to guide the gas sample from the first opening to the second opening. The gas analyzer further includes at least one detector to receive the radiation after traversing the gas sample. The first wall and the second wall of the sampling chamber is curved and at a predetermined distance from each other, an overall shape of the second wall being mostly similar to the first wall. The light source for transmitting at least one of an infrared radiation and a visible radiation forms a ring like radiation pattern with most intensity in a ring area and with less intensity in a middle of the ring.

Various other features, objects, and advantages of the invention will be made apparent to those skilled in art from the accompanying drawings and detailed description thereof.

BRIEF DESCRIPTION OF THE SEVERAL VIEWS OF THE DRAWINGS

FIG. 1 is a cross sectional side view of a gas analyzer in accordance with an embodiment;

FIG. 2 is a perspective view of principal components of the gas analyzer shown in FIG. 1;

FIG. 3 is a cross sectional view of a sampling chamber shown in FIG. 2 in accordance with an embodiment;

FIG. 4 is a cross sectional view of a prior art sampling chamber;

DETAILED DESCRIPTION OF THE INVENTION

Figure 5:
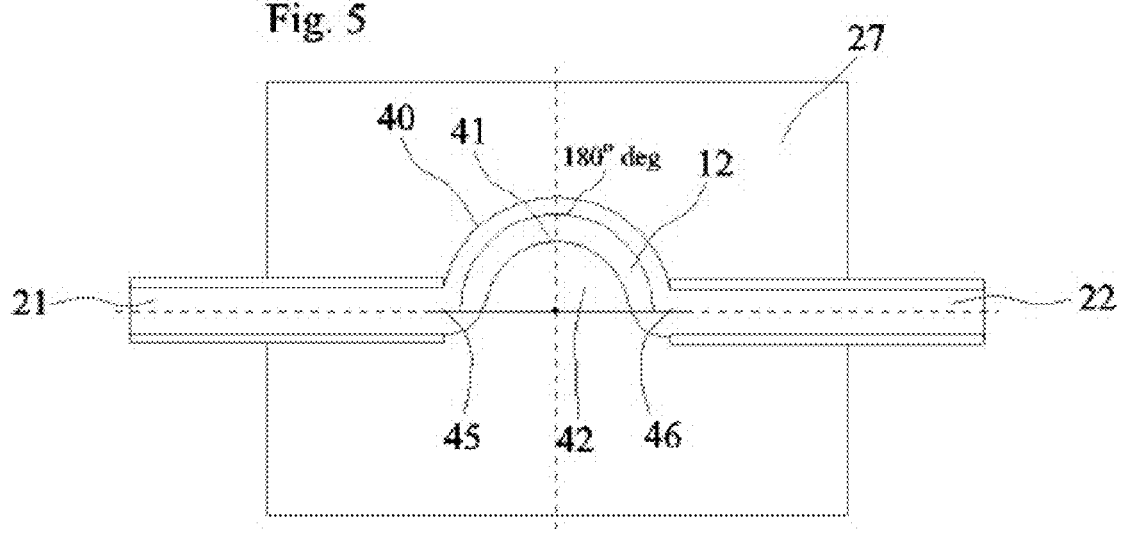
FIG. 5 is a cross sectional view of a sampling chamber in accordance with a second embodiment.

Specific embodiments are explained in the following detailed description making a reference to accompanying drawings. These detailed embodiments can naturally be modified and should not limit the scope of the invention as set fort in the claims.

FIG. 1 shows a cross sectional side view of one type of a gas analyzer 10 comprising a light source 11 for transmitting a radiation towards at least one direction, a sampling chamber 12 and at least one detector 13. In this specific embodiment there is also another detector 14. A number of detectors depend on a number of gas components needed to analyze. The analysis term is used here to cover at least one of a quantitative and qualitative analysis of the gas.

The detectors 13, 14 may be a thermal detector sensitive to a radiation transmitted by the light source 11 towards them. Detectors may be similar each comprising at least one detector channel 15, preferably four separate detector channels, that detect changes in the radiation, which is typically an infrared radiation, but as well a visible radiation is possible depending on the component to be measured, as the radiation traverses through at least one optical window 16 of the sampling chamber 12 and naturally the gas sample inside said sampling chamber, a part of the radiation reflecting from a reflecting surface 17, shown as dashed line in FIG. 1, towards cavities 18, through optical filters 19 to detector channels 15 at the detector 14, and a part of the radiation traversing straight through cavities 20 of the reflecting surface 17 towards the detector channels 15 at the detector 13, through optical filters 19 or similar specifying the desired wave lengths of the radiation to be detected by the separate detector channels 15 of the detector 13. The intensity of the infrared radiation at each gas specific detector channel 15 changes proportionally to the concentration of predetermined specific gases in the sample gas mixture as it flows through the sampling chamber 12. Instead of detector channel there may be separate detectors if such a solution is deemed better.

The light source 11 is in mechanical connection to a radiator 23, which is as shown in FIG. 1 further in connection to a housing 24 made of thermally and electrically conducting material such as metal, but also in connection with an electronics board 25, as well as in connection to a thermal insulator 26 made of for example a plastic, which is further in connection to a housing 27 of the sampling chamber 12 preferably made of a thermally conducting, but also an infrared reflecting material such as metal. The housing 27 of the sampling chamber 12 is further in mechanical connection to a detector body 28 and 29 made of a thermally conducting, but also an infrared reflecting material such as a metal. The reflecting surface 17 is preferably the surface of the detector body 29, which is in connection to the detector body 28. The reflecting surface 17 is polished to reflect the infrared radiation towards the detector 14. The detectors 13, 14 are placed in to detector bodies 28, 29 through elastic o-rings 30 made of a rubber or similar material and sealed with lids 31 made of a thermally conducting material such as metal. Electrical signals from the detectors 13, 14 are transferred through a flexible circuitry 32 to the electronics board 25. Driving an electrical signal to the light source 11 is also transferred through the flexible circuitry 33 from the electronics board 25.

FIG. 2 shows a perspective view of the principal components enabling the functioning of the gas analyzer 10. It is desirable to have the light source 11, which radiation pattern at the reflecting surface 17 is a ring or circular pattern 35 with minimal intensity in the middle, such as a donut like ring, since reflections 36 of the cavities 18 and openings of cavities 20 of the detector channels 15 at the reflecting surface 17 are also positioned in to a circle according to the ring like radiation pattern 35 forming so called imagined donut like shape.

The sampling chamber 12 may comprise a first opening 45 for receiving a gas sample and a second opening 46 for removing the gas sample as shown especially in FIGS. 2 and 3. The inlet tube 21 of the first opening 45 and the outlet tube 22 of the second opening 46 are conically shaped or tapered metal tubes or similar also connected to a further tubing in connection with the gas analyzer (not shown in Figures). As hereinbefore explained referring to FIG. 1 the sampling chamber further may comprise at least one optical window 16, which is towards at least one direction of the radiation of the light source 11. In addition to the at least one optical window 16 there is usually another optical window 16 at a predetermined distance from each other, in which case the radiation traverses both planar optical windows 16 and the gas sample therebetween. If there is exploited a solution with only one optical window 16, then another optical window is usually replaced by a mirror reflecting the radiation back through the only optical window 16 towards the detector.

The sampling chamber 12 may also comprise a first wall 40 and a second wall 41, which are curved and which second wall is opposite to the first wall. The first wall 40 and the second wall 41 are at a predetermined distance from each other varying less than 40%, preferably less than 25% of the overall distance and an overall shape of the second wall 41 is mostly similar to the first wall. The first opening 45 and the second opening 46 separate the first wall 40 from the second wall 41. The sampling chamber 12 may be shaped into a curved cavity between the curved first wall 40 and the curved second wall 41, the sampling chamber 12 having a predetermined length. A main part of this length is formed of a substantially equal cross-sectional area, which is advantageously four-cornered, and also in most cases it is desirable that the distance between the first wall 40 and the second wall 41 is substantially equal in a main part of the length of the sampling chamber 12. Thus the first wall 40, the second wall 41 and both optical windows 16 surround the sampling chamber 12. The optical window 16 is planar towards the radiation to minimize reflections from the window, but the planar window 16 may be crosswise with the radiation curved similarly as the first wall and the second wall.

It is also desirable to have the shape of the curved first wall 40 and the second curved wall 41 of sampling chamber 12 to match with the ring like radiation pattern of the light source 11 especially when the at least one optical window 16 between the first wall 40 and the second wall 41 is arranged to follow the curves of these first and the second walls. The shape of the sampling chamber 12 may be semicircular or circular or almost circular. The reflection at the reflecting surface 17 also locates within the ring or donut like shape radiation pattern. The embodiment shown in FIGS. 2 and 3 reveals a kind of an extension 42 inside the second wall 41 in which case the gas sample flow is guided from the inlet tube 21 through the first opening 45 around the extension 42 through the second opening 46 to the outlet tube 22. The first opening 45 of the inlet tube 21 and the second opening of the outlet tube 22 are on different sides of the extension 42. The distance between the first wall 40 and the second wall 41 is used to maintain the gas sample flow fast and laminar throughout whole the sampling chamber 12 by avoiding any turbulences and mixing of gas samples.

Dotted line 43 in FIG. 2 shows how the radiation traverses through the circular like shaped sampling chamber 12, through the cavity 20 and the optical filter 19 in to one of the four detector channels 15 inside the detector 13. Another dotted line 44 shows how the radiation traverses through the circular like shaped sampling chamber 12, but is then reflected by the reflecting surface 17 towards the detector 14 from the area of the reflection 36, which then traverses through the optical filter 19 in to one of the four detector channels 15 inside the detector 14. As it can be seen from FIG. 2, it is convenient in many ways in addition to what was explained above to have the circular like shaped sampling chamber 12, as well as ring or circular radiation pattern produced by the light source 11 together with the quad channel detector 13, 14. With this construction for example the gas analyzer 10 size is decreased, but the energy efficiency to produce the collimated radiation to the detectors 13, 14 is increased.

It seems that the most suitable shape for the light source 11 measured in term of a size, an energy consumption and a radiation efficiency producing a collimated radiation is a cylindrically shaped parabolic reflector 50 as shown in FIG. 1, which collects and collimates the infrared radiation that the emitter element 51 in the middle of the reflector 50 emits. In the short range of millimeters or a few tens of millimeters the radiation pattern in the imagined plane in front of the source is normally a ring like image with less intensity in the middle of the circular pattern, which is caused by the mechanical construction of the light source 11. In conventional gas analyzers this is a disadvantage since the detector collects the radiation from the middle of the source thus getting less collimated radiation. It is desired that the infrared radiation radiated by the light source 11 is collimated as well as possible since it should traverse the same distance at each point through the gas sample inside the sampling chamber. The radiation with a different than 90° degrees contact angle with the gas inside the sampling chamber causes error to the measured gas concentration and decrease the rise and fall time of the gas analyzer. Also the functioning of optical filters 19 is better with the contact angle close to 90° degrees.

As the light source 11 is cylindrically shaped it is also suitable to arrange separate detector channels 15 in to a cylindrical form in respect to a ring like shaped radiation pattern so that the radiation from the light source 11 is collected as efficiently as possible. An eight detector channel 15 measurement, which means the measurement of eight different gases, can be implemented with two commercial quad channel detectors 13, 14 by placing them in to the gas analyzer 10 as shown in FIG. 1. With this arrangement the pattern of channels created is identical to the shape of the ring like radiation pattern of the light source 11. Also the detectors channels 15 are arranged one after the other matching with the curves of the first wall 40 and/or the second wall 41 of the sampling chamber 12.

FIG. 3 shows a cross sectional view of the sampling chamber 12 in the direction from the source 11 to detector 13. The gas sample enters in to the sampling chamber 12 through a tapered inlet tube 21 that maintains the sampling flow laminar throughout all its length. As described hereinbefore the shape of the curved sampling chamber 12 is like a horseshoe with a rectangular, cross sectional surface area perpendicular to the direction of the gas sample flow. The gas sample flow is maintained constant and laminar throughout all its length and together with a reduced dead space the gas column flowing through the sampling chamber 12 remain unmixed and as stable as possible, but also it maintains its flow speed as fast as possible. The gas sample exits from the sampling chamber through a tapered outlet tube 22, which keeps the exiting gas flow laminar and prevents turbulences at exit. This may also improve the rise/fall time of other preceding analyzers in a larger system.

Dotted lines in FIG. 3 show how the gas sample flows from the first opening 45 of the inlet tube 21 through the sampling chamber 12 and out from the sampling chamber through the second opening 46 of the outlet tube 22. Every step like change in the walls of sampling chamber 12 or elsewhere in the gas sample flow path creates turbulence in to the gas sample flow, which in turn mixes up the columns of different concentration of gas samples thus disturbing the real time concentration measurement of the gases. The connection of inlet tube 21 and outlet tube 22 to the sampling chamber 12 is well fitted and does not generate step like changes to the flow path regardless of small corners between the connections of cylindrical inlet and outlet tubes and rectangular shaped cavity.

In the gas analyzer 10, the extension 42 in the middle of the ring shaped sampling chamber 12 as shown in FIGS. 2 and 3 is imposed in to the middle area of the ring shape radiation pattern with less intensity, whereas the ring shaped sampling chamber 12 is imposed into the middle of the circular or ring shaped radiation pattern with more intensity. In addition the extension 42 in the middle of the ring shaped sampling chamber 12 reflects efficiently the radiation from light source 11 back to the reflector 50 that is skewed or has a contact angle other than 90° degrees in respect to the sampling chamber 12 so that it would not traverse towards the detectors 13, 14, but may be collimated by the reflector 50. The extension 42 of the second wall 41 is between the first opening and the second opening 46 and extends towards the first wall at least as much as a diameter of said first opening 45.

A straight cavity as the sampling chamber for more than one detector channels 15 would be as fast as the ring shaped chamber shown in FIGS. 2 and 3, but it would be difficult to arrange the light source 11 that would be energy and radiation efficient as well as it would produce suitable collimated radiation for all detector channels 15. The ring shaped sampling chamber, as in FIGS. 2 and 3, is thus fast and efficient, but it is also smaller in size, which helps to miniaturize the gas analyzer 10.

The rise/fall time of approximately 40 ms with the gas sample flow of 120 ml/min was measured for the type of the sampling chamber shown in FIGS. 2 and 3. On the other hand the rise/fall time of approximately 190 ms with the gas sample flow of 120 ml/min was measured for the conventional sampling chamber 1 as shown in FIG. 4. Thus the rise and fall time of the sampling chamber 12 as well as the gas analyzer 10 construction shown in FIGS. 1, 2 and 3 is approximately 4-5 times faster compared to the conventional techniques. If the rise/fall time was measured from 0% to 100% level of the analyzer output signal the difference would have been even much greater than that. The total rise/fall time of the gas analyzer 10 described in FIGS. 1, 2 and 3 decreased 40-50% compared to the conventional analyzer construction. As the rise/fall time of the sampling chamber 12 is the most dominant component in respect to the total rise/fall time of the gas analyzer 10 in many applications it is easy to improve the response time of the gas analyzer 10 with the described embodiment.

FIG. 5 shows a second embodiment of the sampling chamber 12 in the housing 27. Fluid flows into the sampling chamber 12 through the inlet tube 21 and exits the sampling chamber 12 through the outlet tube 22. The inlet tube 21 and the outlet tube 22 are in series with a contact angle of 180° degrees between the first opening 45 and the second opening 46. Actually the first openings 45 and the second opening 46 are against each other. The first wall 40 and the second wall 41 of the sampling chamber 12 between the first opening 45 of the inlet tube 21 and the second opening 46 of the outlet tube 22 form a curved cavity having the extension 42 therebetween edging the second wall 41. The extension 42 guides the gas sample flow through the round flow cavity between the first wall 40 and the second wall 41 of the sampling chamber 12. This embodiment of the semicircle sampling chamber is suitable especially when there is a need for fewer than for example eight detector channels 15, as shown in the FIGS. 1, 2 and 3, but more than one detector channel 15 that are used to measure the concentration of the gas sample flowing through the sampling chamber 12. Although the half of the radiation is lost in this FIG. 5 arrangement of the semicircle sampling chamber 12 between the round light source 11 and circularly placed detector channels 15 it is still much more energy efficient construction compared to for example a straight sampling cavity between an array of detector channels and an elongated light source and much faster than the prior art embodiment shown in the FIG. 4.

Figure 6:
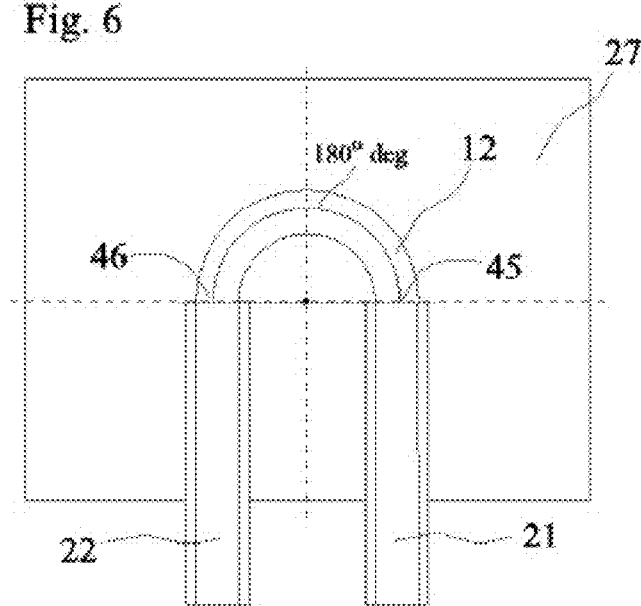
FIG. 6 is a cross sectional view of a sampling chamber in accordance with a third embodiment.

FIG. 6 shows a third embodiment of the sampling chamber 12 in the housing 27. In this arrangement the first opening 45 of the inlet tube 21 and the second opening 46 of the outlet tube 22 are in parallel with a contact angle of 180° degrees. Also in this embodiment the sampling chamber 12 is similarly shaped or curved as in the FIG. 5 embodiment.

The gas analyzer for the measurement of multiple gases in the mixture explained hereinbefore referring to various embodiments of the invention comprising the light source 11, the sampling chamber 12, the reflecting surface 17 and multiple detector channels 15, which reduces the gas analyzer size and decreases the gas analyzer power consumption, increases the energy efficiency as well as produces better detector signal proportional to the measured gas in the mixture, which is achieved with better radiation intensity and more collimated radiation transmitted to multiple detector channels 15. The sampling chamber construction according to the embodiment enables faster rise/fall times for the gas analyzer as known in the prior art, which in turn improves the fast, real time measurement of multiple gases in the gas mixture.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A gas analyzer comprising:
    a light source for transmitting at least one of an infrared radiation and a visible radiation and adapted to form a ring like radiation pattern with most intensity in a ring area and with less intensity in a middle of said ring;
    a sampling chamber having a first opening for receiving a gas sample and having a second opening for removing said gas sample and at least one optical window towards the radiation allowing the radiation to traverse said gas sample and also having a first wall and a second wall opposite to said first wall, said first wall and second wall edging said sampling chamber to guide said gas sample from said first opening to said second opening; and
    at least one detector for receiving the radiation after traversing said gas sample;
    wherein said first wall and said second wall of said sampling chamber is curved and at a predetermined distance from each other, an overall shape of said second wall being mostly similar to said first wall.

2. The gas analyzer according to claim 1, wherein the distance between said first wall and said second wall is substantially equal varying less than 40%, preferably less than 25%.

3. The gas analyzer according to claim 1, wherein said sampling chamber being, shaped into a curved cavity having a predetermined length between said curved first wall and said curved second wall, a main part of said length having a substantially equal cross-sectional area.

4. The gas analyzer according to claim 3, wherein said cross-sectional area is four-cornered.

5. The gas analyzer according to claim 1, wherein in addition to said at least one optical window there is another optical window, which optical windows are planar and at a predetermined distance from each other, allowing the radiation traverse both said optical windows and the gas sample therebetween.

6. The gas analyzer according to claim 5, wherein said both optical windows, said first curved wall and said second curved wall are adapted to surround said sampling chamber having a predetermined length, a main part of said length having a substantially equal cross-sectional area.

7. The gas analyzer according to claim 1, wherein besides said first wall and said second wall also said at least one optical window is edging said sampling chamber, said optical window being planar towards the radiation, but crosswise with said radiation, similarly curved as said first wall and said second wall.

8. The gas analyzer according to claim 1, wherein said light source comprising an emitter element for emitting the radiation and a cylindrically shaped parabolic reflector for collecting and collimating the radiation.

9. The gas analyzer according to claim 1, wherein said first wall and said second wall is curved matching with said ring like radiation pattern of said light source, when said at least one optical window between said first wall and said second wall is adapted to follow curves of said first wall and said second wall.

10. The gas analyzer according to claim 9, wherein said at least one detector comprising various detector channels, each detector channel detecting some specific agent of the gas sample, said detector channels being arranged one after the other matching with said at least one optical window of said sampling chamber.

11. The gas analyzer according to claim 1, wherein said at least one detector comprising various detector channels, each detector channel adapted to detect some specific agent of the gas sample, said detector channels being matched with said ring like radiation pattern of said light source.

12. The gas analyzer according to claim 1, wherein a contact angle of said first opening and said second opening is at least 180 degrees.

13. The gas analyzer according to claim 12, wherein between said first opening and said second opening, said second wall is adapted to form an extension guiding the gas sample around said extension of said second wall from said first opening towards said second opening.

14. The gas analyzer according to claim 13, wherein said extension of said second wall between said first opening and the second opening is adapted to extend towards said first wall at least as much as a diameter of said first opening.

15. A gas analyzer comprising:
a light source for transmitting a radiation towards at least one direction;
a sampling chamber having a first opening adapted to receive a gas sample and having a second opening adapted to remove said gas sample and at least one optical window towards said at least one direction of the radiation adapted to allow the radiation to traverse said gas sample and also having a first wall and a second wall opposite to said first wall, said first wall and second wall adapted to edge said sampling chamber to guide said gas sample from said first opening to said second opening; and
at least one detector adapted to receive said radiation after traversing said gas sample;
wherein said first wall and said second wall of said sampling chamber is curved and at a predetermined distance from each other, an overall shape of said second wall being mostly similar to said first wall and wherein said light source for transmitting at least one of an infrared radiation and a visible radiation is adapted to form a ring like radiation pattern with most intensity in a ring area and with less intensity in a middle of said ring.

16. The gas analyzer according to claim 15, wherein said sampling chamber is semicircular or circular or almost circular.

17. The gas analyzer according to claim 15, wherein said first wall and said second wall is curved matching with said ring like radiation pattern of said light source, when said at least one optical window between said first wall and said second wall is adapted to follow curves of said first wall and said second wall.

18. The gas analyzer according to claim 15, wherein said at least one detector comprising various detector channels, each detector channel adapted to detect some specific agent of the gas sample, said detector channels being matched with said ring like radiation pattern of said light source.

* * * * *